United States Patent [19]

Teach et al.

[11] Patent Number: 4,509,975
[45] Date of Patent: Apr. 9, 1985

[54] META-ANILIDE AND META-ANILIDE UREA HERBICIDAL COMPOUNDS AND METHODS OF USE

[75] Inventors: Eugene G. Teach, El Cerrito; Jeffery T. Springer, El Sobrante, both of Calif.

[73] Assignee: Stauffer Chemical Company, Westport, Conn.

[21] Appl. No.: 567,283

[22] Filed: Dec. 30, 1983

[51] Int. Cl.³ .................. A01N 37/00; A01N 37/44; A01N 47/30; C07C 155/02
[52] U.S. Cl. .................. 71/100; 260/455 A; 560/43; 71/111
[58] Field of Search .................. 260/455 R, 455 A; 564/76; 560/43; 71/100, 111, 120

[56] References Cited

U.S. PATENT DOCUMENTS 4,363,766 12/1982 Bellegarde .................. 260/455 R

Primary Examiner—Henry R. Jiles
Assistant Examiner—Robert C. Whittenbaugh
Attorney, Agent, or Firm—Michael J. Bradley

[57] ABSTRACT

A compound having the structural formula

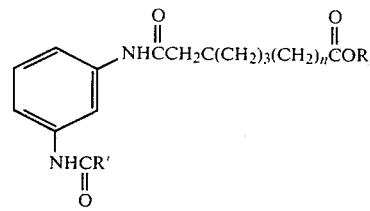

wherein
R is selected from the group consisting of $C_1$–$C_5$ alkyl, preferably methyl; $C_1$–$C_3$ haloalkyl, preferably $C_2$-haloalkyl and most preferably trifluoromethyl; aryl, preferably phenyl, $C_2$–$C_8$ alkoxyalkyl, preferably ethoxyethyl and ethoxyethoxyethyl;
R' is selected from the group consisting of $C_2$–$C_8$ alkyl, preferably $C_2$–$C_3$ alkyl; $C_1$–$C_3$ alkoxy, preferably methoxy; cyclopropyl; methacryl; $C_1$–$C_3$ alkylmercapto, preferably methylmercapto; methylamino; ethylamino; $C_2$–$C_4$ dialkylamino, preferably dimethylamino; $C_2$–$C_4$ alkylalkoxyamino, preferably methylmethoxyamino; and
n equals the integer 0 or 1.

25 Claims, No Drawings

META-ANILIDE AND META-ANILIDE UREA HERBICIDAL COMPOUNDS AND METHODS OF USE

BACKGROUND OF THE INVENTION

The present invention relates to certain meta-anilide and meta-anilide urea compounds which are useful as herbicides and particularly useful as post-emergent herbicides against annual and perennial grasses and broadleaf weeds.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

THE PRIOR ART

U.S. Pat. Nos. 3,642,891, 3,723,474 and 3,941,581 disclose related anilide ureas but fail to disclose the manufacture and use of anilide ureas having branched-alkyl esters.

Efforts are constantly being made, however, to find compounds which are equal to or greater in effectiveness than presently existing compounds, or which are more economical to produce.

DESCRIPTION OF THE INVENTION

This invention relates to the production of novel meta-anilide and meta-anilide urea compounds and their use as herbicides. The novel compounds of this invention have the following structural formula

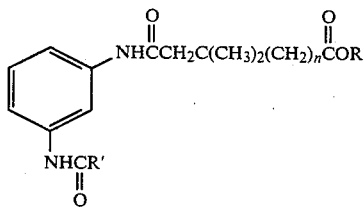

wherein
  R is selected from the group consisting of $C_1$–$C_5$ alkyl, preferably methyl; $C_1$–$C_3$ haloalkyl, preferably $C_2$-haloalkyl and most preferably trifluoromethyl; aryl, preferably phenyl; $C_2$–$C_8$ alkoxyalkyl, preferably ethoxyethyl and ethoxyethoxyethyl;
  R' is selected from the group consisting of $C_2$–$C_8$ alkyl, preferably $C_2$–$C_3$ alkyl; $C_1$–$C_3$ alkoxy, preferably methoxy; cyclopropyl; methacryl; $C_1$–$C_3$ alkylmercapto, preferably methylmercapto; methylamino, ethylamino; $C_2$–$C_4$ dialkylamino, preferably dimethylamino; $C_2$–$C_4$ alkylalkoxyamino, preferably methylmethoxyamino; and
  n equals the integer 0 or 1.

In the above description of the compounds of this invention, alkyl includes both straight- and branched-chain configurations; for example, methyl, ethyl, n-propyl, isopropyl, n-butyl, sec-butyl, isobutyl, tert-butyl, and similar isomers of the higher alkyls.

The compounds of the invention can be produced in a multi-step process in accordance with the following generalized sequence of steps. R, R' and n are as defined above.

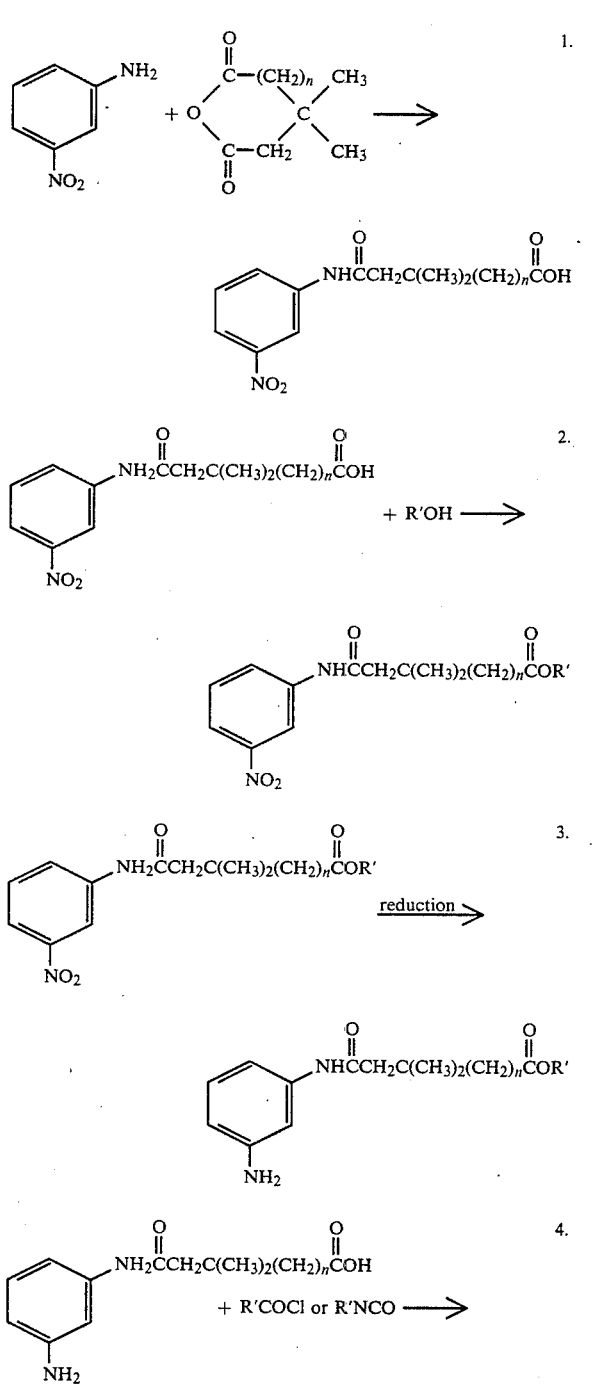

-continued

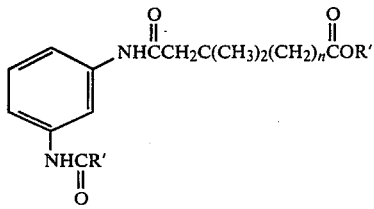

All compounds of this invention can be made by the above reaction scheme except when R' is a disubstituted amino group. When R' is a disubstituted amino group step (1) would be modified to use a properly substituted aniline:

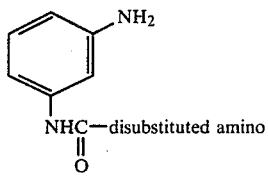

rather than

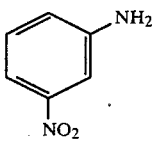

as starting material and the preparation requires only step (1) and (2) reactions.

The compounds of this invention can be prepared using the following method:

3-Nitroaniline is dissolved in tetrahydrofuran (or other dry solvent) at room temperature with stirring. An appropriate anhydride to produce the desired product dissolved in tetrahydrofuran is then added to this solution and reacted at room temperature and then refluxed for about thirty minutes to assure completion of the reaction. The mixture is concentrated by rotary evaporation, leaving the carboxylic acid anilide in yields of acceptable quantity. The carboxylic acid is esterified by refluxing in about a five-fold excess of the necessary alcohol to produce the desired product. A catalyst amount of methane sulfonic acid reduces reaction time and improves yield. After the mixture is refluxed a minimum of four hours to assure completion of the reaction, the product is obtained by rotary evaporation. The aromatic nitro group is reduced by using the art-recognized iron powder-hydrochloric acid method. The resulting substituted aniline is acylated at room temperature in methylene chloride (or other solvent) to yield the title compounds.

The end product compounds can be produced by selecting any one of the compounds produced in accordance with steps 1, 2, 3 or 4 above and continuing the reaction sequence as indicated.

Examples 1 and 2 below illustrate various methods of making the compounds of the invention using various starting materials. All intermediates and final products are identified by infrared, nuclear magnetic resonance and proton magnetic resonance spectra.

EXAMPLE I

Preparation of Methyl-N-(3-propionamidophenyl)-2,2-dimethyl succinamate

Step 1

3-Nitroaniline (27.6 grams (g)) was dissolved by stirring in 200 milliliters (ml) tetrahydrofuran. 2,2-Dimethyl succinic anhydride (25.6 g) in some tetrahydrofuran was added dropwise with stirring. The reaction was stirred at room temperature for four hours. The reaction product was recovered by addition of 500 ml ethyl acetate, followed by three washings with 3% hydrochloric acid and one with distilled water. The solution was dried with sodium sulfate and rotary evaporated to yield 50.2 g of N-(3-nitrophenyl)-2,2-dimethylsuccinamic acid.

Step 2

Twenty-five g N-(3-nitrophenyl)-2,2-dimethylsuccinamic acid from step (1) was added to a solution of 250 ml methanol and 5 drops methane sulfonic acid. The mixture was stirred and allowed to reflux for six hours. When the reaction was cooled to 20° C. it was dried using sodium sulfate. Rotary evaporation yields 23.7 g of methyl-N-(3-nitrophenyl)-2,2-dimethyl succinamate.

Step 3

Fifty-two ml ethanol and 43 ml water are combined with 14.4 g powdered iron. As mechanical stirring was begun 1.1 ml concentrated hydrochloric acid was added and the mixture taken to reflux. When reflux was attained the heat source was removed and 24 g methyl-N-(3-nitrophenyl)-2,2-dimethyl succinamate from step (2) above is added at a rate that maintains reflux. When reflux stops 1.3 g 50% sodium hydroxide was added with vigorous stirring. The reaction product was filtered through 1″ dicalite pad and then concentrated by rotary evaporation. The product was extracted with ethyl acetate and washed 3 times with water. The reaction product was dried and colorized with sodium sulfate and florisil. Rotary evaporation yields 19.3 grams of methyl-N(3-aminophenyl)-2,2-dimethylsuccinamate.

Step 4

Two g methyl-N-(3-aminophenyl)-2,2-dimethyl succinimate from step (3) above and 0.81 g triethylamine are combined in 100 ml ethyl acetate that was stirred at −5° C. Propionyl chloride (0.76 g) in 10 ml ethyl acetate is added dropwise and stirred at 20° C. for three hours. The mixture was washed three times with water and then dried with sodium sulfate. Rotary evaporation yields 2.2 g of methyl-N-(3-propionamidophenyl)-2,2-dimethyl succinamate. This compound will be referred to as Compound No. 6.

EXAMPLE 2

Preparation of Methyl-N-(3-dimethylureidophenyl)-2,2-dimethyl succinamate

Step 1

12.5 g (3-dimethylureido)aniline was dissolved by stirring in 150 ml tetrahydrofuran. Nine g 2,2-dimethylsuccinic anhydride in 30 ml tetrahydrofuran was added dropwise with stirring. The reaction was stirred at room temperature for four hours. The reaction product was recovered by addition of 200 ml ethyl acetate, followed by three washings with 3% hydrochloric acid and one with distilled water. The solution was dried with sodium sulfate and rotary evaporated to yield 10.2 g of N-(3-dimethylureidophenyl)-2,2-dimethyl succinamic acid.

Step 2

Ten g N-(3-dimethylureidophenyl)-2,2-dimethyl succinamic acid from step (1) was added to a solution of 275 ml methanol and 5 drops methane sulfonic acid. The mixture was stirred and allowed to reflux for 45 minutes. When the reaction has cooled to 20° C. it was dried using sodium sulfate. Rotary evaporation yields 10.3 g of methyl-N-(3-dimethylureidophenyl)-2,2-dimethyl succinamate. This compound will be referred to as Compound No. 3.

The following is a table of certain selected compounds that are preparable according to the procedure described herein. Compound numbers are assigned to each compound and are used throughout the remainder of the application.

TABLE I

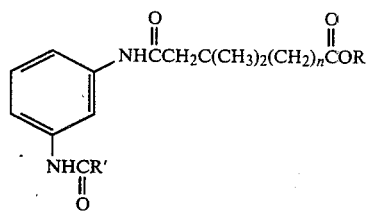

| Cmpd. No. | R | R' | n | $n_D^{30}$ or melting point |
|---|---|---|---|---|
| 1 | —CH$_2$CH$_3$ | —NHCH$_3$ | 1 | waxy solid |
| 2 | —CH$_3$ | —NHCH$_3$ | 1 | waxy solid |
| 3 | —CH$_3$ | —N(CH$_3$)$_2$ | 1 | 1.5379 |
| 4 | —CH$_2$CH$_3$ | —N(CH$_3$)$_2$ | 1 | 1.5262 |
| 5 | —CH$_2$CH$_3$ | —CH$_2$CH$_3$ | 1 | 86.0–91.0 |
| 6 | —CH$_3$ | —CH$_2$CH$_3$ | 1 | 80.0–85.0 |
| 7 | —CH$_3$ | —OCH$_3$ | 1 | 1.5300 |
| 8 | —CH$_3$ | —SCH$_3$ | 1 | 1.5664 |
| 9 | —CH$_3$ | —C(CH$_3$)=CH$_2$ | 1 | waxy solid |
| 10 | —CH$_3$ | —CH(CH$_2$CH$_2$) (cyclopropyl) | 1 | waxy solid |
| 11 | —CH$_3$ | —C(CH$_3$)$_2$CH$_2$CH$_2$CH$_2$ | 1 | 1.5225 |
| 12 | —CH$_3$ | —CH(CH$_3$)CH$_2$CH$_2$CH$_2$ | 1 | 1.5221 |
| 13 | —CH$_3$ | —N(CH$_3$)OCH$_3$ | 1 | 1.5446 |
| 14 | —CH$_2$CH$_3$ | —N(CH$_3$)OCH$_3$ | 1 | 1.5402 |
| 15 | —CH$_2$CH$_2$CH$_3$ | —CH$_2$CH$_3$ | 1 | 78.0–80.0 |
| 16 | —CH$_2$CH$_2$CH$_3$ | —N(CH$_3$)$_2$ | 1 | 1.5242 |
| 17 | —CH$_3$ | —CH$_2$CH$_3$ | 0 | 1.5492 |
| 18 | —CH$_3$ | —SCH$_3$ | 0 | 1.5789 |
| 19 | —CH$_3$ | —OCH$_3$ | 0 | 1.5463 |
| 20 | —CH$_2$CH$_2$CH$_3$ | —NHCH$_3$ | 1 | 1.5376 |
| 21 | —CH$_2$CH$_2$CH$_3$ | —SCH$_3$ | 1 | 1.5554 |
| 22 | —CH$_2$CH$_2$CH$_3$ | —OCH$_3$ | 1 | 1.5282 |
| 23 | —CH$_2$CH$_2$CH$_3$ | —CH(CH$_2$CH$_2$) (cyclopropyl) | 1 | 84.0–88.0 |
| 24 | —CH$_2$CH$_2$CH$_3$ | —C(CH$_3$)=CH$_2$ | 1 | 1.0384 |
| 25 | —C(CH$_3$)$_3$ | —CH$_2$CH$_3$ | 1 | 85.0–88.0 |
| 26 | —CH$_3$ | —NHCH$_3$ | 0 | 72.0–76.0 |
| 27 | —C$_6$H$_{11}$ (cyclohexyl) | —N(CH$_3$)$_2$ | 1 | 1.5676 |
| 28 | —C$_6$H$_{11}$ (cyclohexyl) | —NHCH$_3$ | 1 | 1.5760 |

TABLE I-continued

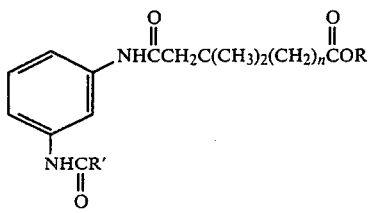

| Cmpd. No. | R | R' | n | $n_D^{30}$ or melting point |
|---|---|---|---|---|
| 29 | —CH$_2$CF$_3$ | —N(CH$_3$)$_2$ | 1 | 1.4509 |
| 30 | —CH$_2$CF$_3$ | —NHCH$_3$ | 1 | 85.0–88.0 |
| 31 | —CH$_2$CF$_3$ | —NCH$_3$(OCH$_3$) | 1 | 1.4916 |
| 32 | —CH$_2$CF$_3$ | —CH$_2$CH$_3$ | 1 | 70.0–76.0 |
| 33 | —CH$_2$CH$_2$CH$_3$ | —NCH$_3$(OCH$_3$) | 1 | 1.5280 |
| 34 | —C$_6$H$_{11}$ (cyclohexyl) | —CH$_2$CH$_3$ | 1 | 97.0–98.0 |
| 35 | —CH$_2$CH$_3$ | —C(CH$_3$)$_2$CH$_2$CH$_2$CH$_3$ | 1 | 1.5183 |
| 36 | —CH$_2$CH$_2$CH$_3$ | —C(CH$_3$)$_2$CH$_2$CH$_2$CH$_3$ | 1 | 1.5106 |
| 37 | —CH$_2$CH$_2$OCH$_2$CH$_2$OCH$_2$CH$_3$ | —N(CH$_3$)$_2$ | 1 | 1.5129 |
| 38 | —CH$_2$CH$_2$OCH$_2$CH$_2$OCH$_2$CH$_3$ | —C(CH$_3$)$_2$CH$_2$CH$_2$CH$_2$ | 1 | 1.5144 |
| 39 | —CH$_2$CH$_2$OCH$_2$CH$_2$OCH$_2$CH$_3$ | —SCH$_3$ | 1 | 1.5523 |
| 40 | —CH$_2$CH$_2$OCH$_2$CH$_2$OCH$_2$CH$_3$ | —CH(CH$_2$)$_{10}$(CH$_2$) (cyclopropyl-type) | 1 | 1.5386 |
| 41 | —CH$_2$CH$_2$OCH$_2$CH$_2$OCH$_2$CH$_3$ | —C(CH$_3$)=CH$_2$ | 1 | 1.5374 |
| 42 | —CH$_3$ | —N(CH$_3$)$_2$ | 0 | 1.5401 |

Herbicidal Screening Tests

As previously mentioned, the herein described compounds produced in the above-described manner are phytotoxic compounds which are useful and valuable in controlling various plant species. Selected compounds of this invention were tested as herbicides in the following manner.

Pre-emergence herbicide test

On the day preceding treatment, seeds of seven different grass and broadleaf weed species are planted in loamy sand soil in individual rows in 6×10×3 inch flats. The seeds used are green foxtail (FT) (*Setaria viridis*), watergrass (WG) (*Echinochloa crusgalli*), wild oat (WO) (*Avena fatua*), annual morningglory (AMG) (*Ipomoea purpurea*), velvetleaf (VL) (*Abutilon theophrasti*), Indian mustard (MD) (*Brassica kaber*), and curley dock (CD) (*Rumex crispus*).

The flats are placed in the greenhouse, watered daily (both before and after chemical treatment) with a sprinkler and maintained at about 78° F. Chemical spray treatment is prepared by weighing out 333 mg of compound and dissolving in 25 ml acetone containing 1% polyoxyethylene sorbitan monolaurate emulsifier. From this stock solution 18 ml are removed and brought up to a 40 ml volume with a 19:1 water/acetone mixture. The carrier volume is 80 gallons/acre (748L/ha) and a 4 lbs/acre rate (4.48 kg/ha) is used.

Twelve to fourteen days after treatment, the degree of injury or control is determined by comparison with untreated check plants of the same age. The injury rating from 0 to 100% is recorded for each species as percent control with 0% representing no injury and 100% representing complete control.

The results of the tests are shown in the following Table II.

TABLE II

Pre-Emergence Herbicidal Activity
Application Rate - 4.48 kg/ha

| Cmpd. No. | FT | WG | WO | AMG | VL | MD | CD | AVE GR | AVE BL |
|---|---|---|---|---|---|---|---|---|---|
| 1 | 0 | 0 | 0 | 0 | 0 | 0 | 0 | 0 | 0 |
| 2 | 10 | 20 | 0 | 20 | 20 | 30 | 0 | 10 | 18 |
| 3 | 20 | 30 | 20 | 75 | 85 | 85 | 65 | 23 | 78 |
| 4 | 20 | 10 | 0 | 10 | 20 | 95 | 65 | 10 | 48 |
| 5 | 0 | 0 | 0 | 0 | 0 | 60 | 85 | 0 | 36 |
| 6 | 10 | 10 | 0 | 0 | 0 | 60 | 85 | 7 | 36 |
| 7 | 10 | 20 | 0 | 55 | 65 | 85 | 80 | 10 | 71 |

TABLE II-continued

Pre-Emergence Herbicidal Activity
Application Rate - 4.48 kg/ha

| Cmpd. No. | FT | WG | WO | AMG | VL | MD | CD | AVE GR | AVE BL |
|---|---|---|---|---|---|---|---|---|---|
| 8 | 85 | 80 | 20 | 45 | 0 | 100 | 100 | 62 | 61 |
| 9 | 65 | 45 | 0 | 50 | 50 | 90 | 100 | 37 | 73 |
| 10 | 0 | 0 | 0 | 0 | 0 | 20 | 30 | 0 | 13 |
| 11 | 0 | 0 | 0 | 0 | 65 | 75 | 75 | 0 | 54 |
| 12 | 0 | 0 | 0 | 0 | 0 | 90 | 75 | 0 | 41 |
| 13 | 100 | 100 | 60 | 65 | 95 | 95 | 100 | 87 | 89 |
| 14 | 100 | 100 | 65 | 70 | 100 | 100 | 100 | 88 | 93 |
| 15 | 0 | 0 | 0 | 0 | 0 | 0 | 0 | 0 | 0 |
| 16 | 0 | 0 | 0 | 0 | 0 | 0 | 0 | 0 | 0 |
| 17 | 60 | 60 | 45 | 60 | 60 | 90 | 90 | 55 | 75 |
| 18 | 30 | 20 | 70 | 70 | 60 | 100 | 100 | 40 | 83 |
| 19 | 20 | 0 | 15 | 65 | 60 | 65 | 90 | 12 | 70 |
| 20 | 0 | 0 | 0 | 0 | 0 | 50 | 0 | 0 | 12 |
| 21 | 0 | 0 | 0 | 0 | 0 | 40 | 0 | 0 | 10 |
| 22 | 0 | 0 | 0 | 0 | 0 | 50 | 0 | 0 | 12 |
| 23 | 0 | 0 | 0 | 0 | 0 | 50 | 0 | 0 | 12 |
| 24 | 0 | 0 | 0 | 0 | 0 | 0 | 0 | 0 | 0 |
| 25 | 0 | 0 | 0 | 0 | 0 | 0 | 0 | 0 | 0 |
| 26 | 50 | 25 | 0 | 90 | 80 | 90 | 95 | 25 | 89 |
| 27 | — | 0 | 0 | 75 | 70 | 30 | — | 0 | 23 |
| 28 | — | 0 | 0 | 20 | 20 | 30 | — | 0 | 23 |
| 29 | 0 | 0 | 0 | 5 | 0 | 5 | — | 0 | 3 |
| 30 | — | 0 | 0 | 0 | 0 | 10 | — | 0 | 3 |
| 31 | 0 | 0 | 0 | 45 | 30 | 30 | — | 0 | 35 |
| 32 | 0 | 0 | 0 | 0 | 0 | 30 | — | 0 | 10 |
| 33 | 0 | 0 | 0 | 0 | 0 | 0 | — | 0 | 0 |
| 34 | 0 | 0 | 0 | 20 | 15 | 50 | 0 | 0 | 21 |
| 35 | — | 0 | 0 | 0 | 0 | 95 | 90 | 0 | 47 |
| 36 | 0 | 0 | 0 | 0 | 0 | 0 | 0 | 0 | 0 |
| 37 | 0 | 0 | 0 | 0 | 0 | 0 | 0 | 0 | 0 |
| 38 | 0 | 0 | 0 | 0 | 0 | 0 | 0 | 0 | 0 |
| 39 | 0 | 0 | 0 | 0 | 0 | 0 | 0 | 0 | 0 |
| 40 | 0 | 0 | 0 | 0 | 40 | 30 | 0 | 0 | 18 |
| 41 | 0 | 0 | 0 | 0 | 0 | 0 | 0 | 0 | 0 |
| 42 | 60 | 50 | 40 | 95 | 100 | 50 | 90 | 50 | 84 |

AVE GR = The average of all grass weeds treated at the application rate.
AVE BL = The average of all broadleaf weeds treated at the application rate.

Post-Emergence Herbicide Test

This test is conducted in an identical manner to the testing procedure for the pre-emergence herbicide test, except the seeds of the seven different grass and broadleaf weed species are planted 12 days before treatment. Also, watering of the treated flats is confined to the soil surface and not to the foliage of the sprouted plants.

The results of the post-emergence herbicide test are reported in Table III.

TABLE III

Post-Emergence Herbicidal Activity
Application Rate - 4.48 kg/ha

| Cmpd. No. | FT | WG | WO | AMG | VL | MD | CD | AVE GR | AVE BL |
|---|---|---|---|---|---|---|---|---|---|
| 1 | 100 | 100 | 100 | 100 | 100 | 100 | 100 | 100 | 100 |
| 2 | 100 | 100 | 100 | 100 | 100 | 100 | 100 | 100 | 100 |
| 3 | 100 | 100 | 60 | 100 | 100 | 100 | 100 | 87 | 100 |
| 4 | 100 | 85 | 55 | 95 | 100 | 100 | 100 | 83 | 99 |
| 5 | 95 | 80 | 30 | 100 | 100 | 100 | 100 | 68 | 100 |
| 6 | 100 | 90 | 85 | 100 | 100 | 100 | 100 | 92 | 100 |
| 7 | 90 | 65 | 85 | 95 | 100 | 100 | 100 | 80 | 99 |
| 8 | 100 | 100 | 95 | 100 | 95 | 100 | 100 | 98 | 99 |
| 9 | 100 | 75 | 65 | 100 | 100 | 100 | 100 | 80 | 100 |
| 10 | 65 | 65 | 75 | 95 | 95 | 100 | 100 | 68 | 98 |
| 11 | 75 | 45 | 60 | 90 | 100 | 100 | 100 | 60 | 98 |
| 12 | 45 | 35 | 50 | 75 | 100 | 100 | 100 | 43 | 94 |
| 13 | 100 | 100 | 95 | 95 | 95 | 100 | 100 | 98 | 98 |
| 14 | 100 | 100 | 100 | 100 | 100 | 100 | 100 | 100 | 100 |
| 15 | 0 | 90 | 30 | 50 | 70 | 100 | 0 | 40 | 55 |
| 16 | 70 | 20 | 70 | 65 | 80 | 100 | 90 | 53 | 84 |
| 17 | 40 | 20 | 40 | 75 | 85 | 100 | 90 | 33 | 88 |
| 18 | 90 | 75 | 75 | 90 | 95 | 100 | 100 | 80 | 96 |
| 19 | 40 | 20 | 20 | 40 | 70 | 75 | 90 | 27 | 69 |
| 20 | 20 | 20 | 0 | 65 | 90 | 100 | 100 | 13 | 89 |
| 21 | 75 | 80 | 0 | 65 | 100 | 100 | 70 | 52 | 84 |
| 22 | 10 | 20 | 0 | 60 | 100 | 100 | 100 | 13 | 90 |
| 23 | 60 | 40 | 20 | 10 | 75 | 100 | 100 | 40 | 71 |
| 24 | 65 | 20 | 0 | 75 | 100 | 95 | 100 | 28 | 93 |
| 25 | 75 | 65 | 20 | 50 | 20 | 100 | 90 | 53 | 65 |
| 26 | 50 | 75 | 85 | 90 | 100 | 100 | 100 | 70 | 98 |

TABLE III-continued

Post-Emergence Herbicidal Activity
Application Rate - 4.48 kg/ha

| Cmpd. No. | FT | WG | WO | AMG | VL | MD | CD | AVE GR | AVE BL |
|---|---|---|---|---|---|---|---|---|---|
| 27 | 40 | 0 | 30 | 80 | 50 | 90 | 0 | 23 | 55 |
| 28 | 0 | 0 | 20 | 40 | 45 | 100 | 0 | 7 | 46 |
| 29 | 20 | 20 | 15 | 70 | 100 | 90 | 100 | 18 | 90 |
| 30 | 95 | 0 | 40 | 85 | 90 | 100 | 90 | 45 | 91 |
| 31 | 95 | 20 | 20 | 80 | 20 | 85 | 100 | 45 | 71 |
| 32 | 60 | 20 | 35 | 80 | 100 | 100 | 100 | 38 | 95 |
| 33 | 95 | 20 | 20 | 100 | 100 | 100 | 100 | 45 | 100 |
| 34 | 10 | 10 | 0 | 40 | 15 | 90 | 50 | 7 | 49 |
| 35 | 80 | 45 | 5 | 45 | 100 | 95 | 100 | 43 | 85 |
| 36 | 95 | 80 | 0 | 35 | 0 | 100 | 0 | 58 | 35 |
| 37 | 50 | 20 | 20 | 45 | 50 | 40 | 40 | 30 | 35 |
| 38 | 10 | 20 | 10 | 20 | 45 | 50 | 20 | 13 | 34 |
| 39 | 60 | 35 | 30 | 40 | 50 | 95 | 80 | 42 | 66 |
| 40 | 10 | 0 | 20 | 40 | 40 | 40 | 30 | 10 | 38 |
| 41 | 0 | 0 | 0 | 20 | 0 | 0 | 0 | 0 | 5 |
| 42 | 40 | 40 | 85 | 100 | 100 | 100 | 80 | 55 | 95 |

AVE GR = The average of all grass weeds treated at the application rate.
AVE BL = The average of all broadleaf weeds treated at the application rate.

The compounds of the present invention are useful as herbicides, especially as post-emergence herbicides, and can be applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for pre-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifier concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active ingredient by weight of the herbicidal composition.

Granular formulations wherein the toxicant is carried on relatively coarse particles, are usually applied without dilution to the area in which suppression of vegetation is desired. Typical carriers of granular formulations include sand, fuller's earth, bentonite clays, vermiculite, perlite and other organic or inorganic materials which absorb or which may be coated with the toxicant. Granular formulations normally are prepared to contain about 5% to about 25% of active ingredients which may include surface-active agents such as wetting agents, dispersing agents or emulsifiers; oil such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporating application.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | | | |
|---|---|---|---|
| Oil | | | |
| Ingredient | Weight % | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for herbicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers and other herbicides, pesticides and the like, used as adjuvant or in combination with any of the above-described adjuvants. Other phytotoxic compounds useful in combination with the abovedescribed compounds include, for example, 2,4-dichlorophenoxyacetic acids, 2,4,5-trichlorophenoxyacetic acid, 2-methyl-4-chlorophenoxyacetic acid and the salts, esters and amides thereof, triazine derivatives, such as 2,4-bis(3-methoxypropylamino)-6-methylthio-s-triazine, 2-chloro-4-ethylamino-6-isopropylamino-s-triazine, and 2-ethylamino-4-isopropyl-amino-6-methyl-mercapto-s-triazine; urea derivatives, such as 3-(3,5-dichlorophenyl)-1,1-dimethylurea and 3-(p-chlorophenyl)-1,1-dimethylurea; and acetamides such as N,N-diallyl-α-chloroacetamide, and the like; benzoic acids such as 3-amino-2,5-dichlorobenzoic acid; thiocarbamates such as S-propyl N,N-dipropylthiocarbamate, S-ethyl N,N-dipropyl thiocarbamate, S-ethyl cyclohexylethylthiocarbamate, S-ethyl hexahydro-1H-azepine-1-carbothioate and the like; anilines such as 4-(methylsulfonyl)-2,6-dinitro-N,N-substituted aniline, 4-trifluoromethyl-2,6-dinitro-N,N-di-n-propyl aniline, 4-trifluoromethyl-2,6-dinitro-N-ethyl-N-butyl aniline, 2-[4-(2,4-dichlorophenoxy)phenoxy]propanoic acid, 2-[1-(ethoxyimino)butyl]-5-[2-ethylthio)propyl]-3-hydroxy-2-cyclohexene-1-one, (±)-butyl-2[4-[(5-trifluoromethyl)-2-pyridinyl)oxy]phenoxy]propanate, sodium 5-[2-chloro-4-(trifluoromethyl)phenoxy]-2-nitrobenzoate, 3-isopropyl-1H-2,1,3benzothiadiazine-4(3H)-one-2,2-dioxide, and 4-amino-6-tertbutyl-3(methylthio)-as-triazin-5(4H)-one or (4-amino-6-(1,1-dimethylethyl)-3(methylthio)-1,2,4-triazin-5(4H)-one). Fertilizers useful in combination with the active ingredients include, for example, ammonium nitrate, urea and superphosphate. Other useful additaments include materials in which plant organisms take root and grow such as compost, manure, humus, sand, and the like.

We claim:

1. A compound having the structural formula

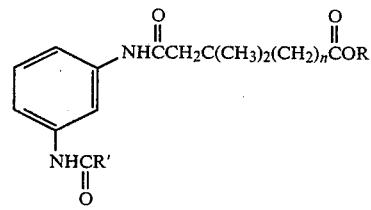

wherein

R is selected from the group consisting of $C_1$-$C_5$ alkyl, $C_1$-$C_3$ haloalkyl, phenyl and $C_2$-$C_8$ alkoxyalkyl;

R' is selected from the group consisting of $C_2$-$C_8$ alkyl, $C_1$-$C_3$ alkoxy, cyclopropyl, methacryl, $C_1$-$C_3$ alkylmercapto, methylamino, ethylamino, $C_2$-$C_4$ dialkylamino, and $C_2$-$C_4$ alkylalkoxyamino; and n equals the integer 0 or 1.

2. The compound of claim 1 R is $C_1$-$C_3$ alkyl; and R' is methoxy.

3. The compound of claim 1 wherein R is methyl, R' is methoxy and n is 1.

4. The compound of claim 1 wherein R is ethyl, R' is methoxy and n is 1.

5. The compound of claim 1 wherein R is methyl, R' is dimethylamino and n is 1.

6. The compound of claim 1 wherein R is ethyl, R' is dimethylamino and n is 1.

7. The compound of claim 1 wherein R is methyl, R' is methylmercapto and n is 1.

8. The compound of claim 1 wherein R is ethyl, R' is methylmethoxyamino and n is 1.

9. The compound of claim 1 wherein R is methyl, R' methylmercapto and n is 0.

10. The compound of claim 1 wherein R is methyl, R' is ethoxy and n is 0.

11. The compound of claim 1 wherein R is propyl, R' is methylmethoxyamino and n is 1.

12. The compound of claim 1 wherein R is methyl, R' is di methylamino and n is 1.

13. A herbicidal composition comprising an herbicidally effective amount of a compound having the structural formula

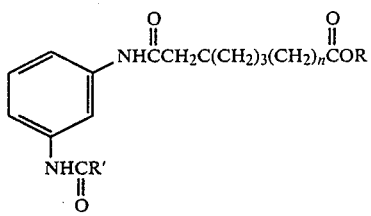

wherein
R is selected from the group consisting of $C_1$–$C_5$ alkyl, $C_1$–$C_3$ haloalkyl, phenyl and $C_2$–$C_8$ alkoxyalkyl;
R' is selected from the group consisting of $C_2$–$C_8$ alkoxy, $C_1$–$C_3$ alkoxy, cyclopropyl, methacryl, $C_1$–$C_3$ alkylmercapto, methylamino, ethylamino, $C_2$–$C_4$ dialkylamino, and $C_2$–$C_4$ alkylalkoxyamino, and;
n equals the integer 0 or 1; an inert carrier.

14. The method of controlling undesirable vegetation comprising applying to the area where control is desired, an herbicidally effective amount of a compound having the formula

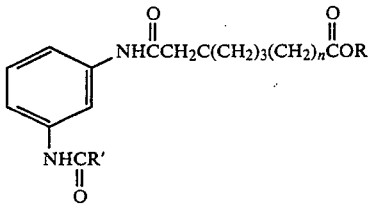

wherein
R is selected from the group consisting of $C_1$–$C_5$ alkyl, $C_1$–$C_3$ haloalkyl, phenyl and $C_2$–$C_8$ alkoxyalkyl;
R' is selected from the group consisting of $C_2$–$C_8$ alkyl, $C_1$–$C_3$ alkoxy, cyclopropyl, methacryl, $C_1$–$C_3$ alkylmercapto, methylamino, ethylamino, $C_2$–$C_4$ dialkylamino, and $C_2$–$C_4$ alkylalkoxyamino; and
n equals the integer 0 or 1.

15. The method of claim 14 wherein R is $C_1$–$C_3$ alkyl and R' is methoxy.

16. The method of claim 14 wherein R is methyl, R' is methoxy and n is 1.

17. The method of claim 14 wherein R is ethyl, R' is methoxy and n is 1.

18. The method of claim 14 wherein R is methyl, R' is dimethylamino and n is 1.

19. The method of claim 14 wherein R is ethyl, R' is dimethylamino and n is 1.

20. The method of claim 14 wherein R is methyl, R' is methylmercapto and n is 1.

21. The method of claim 14 wherein R is ethyl, R' is methylmethoxyamino and n is 1.

22. The method of claim 14 wherein R is methyl, R' methylmercapto and n is 0.

23. The method of claim 14 wherein R is methyl, R' is ethoxy and n is 0.

24. The method of claim 14 wherein R is propyl, R' is methylmethoxyamino and n is 1.

25. The method of claim 14 wherein R is methyl, R' is dimethylamino and n is 1.

* * * * *